United States Patent [19]

Lion et al.

[11] Patent Number: 5,587,145
[45] Date of Patent: Dec. 24, 1996

[54] AQUEOUS AEROSOL LACQUER FOR SETTING HAIR

[75] Inventors: Bertrand Lion, Livry-Gargan; Jean Mondet, Drancy; Christine Dupuis, Paris, all of France

[73] Assignee: L'Oreal, Paris, France

[21] Appl. No.: 195,145

[22] Filed: Feb. 14, 1994

[30] Foreign Application Priority Data

Feb. 16, 1993 [FR] France .................................. 93 01724

[51] Int. Cl.⁶ .............................. A61K 7/11; A61K 9/12
[52] U.S. Cl. ..................... 424/45; 424/47; 424/70.11; 424/DIG. 1; 424/DIG. 2; 424/78.08; 424/70.1; 514/957
[58] Field of Search ................... 424/43, 45, 70, 424/71, DIG. 1, 78.08, 47, 70.11, 70.1; 514/957

[56] References Cited

U.S. PATENT DOCUMENTS

| | | | |
|---|---|---|---|
| 3,972,336 | 8/1976 | Nowak, Jr. et al. | 424/DIG. 1 |
| 4,288,427 | 9/1981 | Farmer, III et al. | 424/45 |
| 5,094,838 | 3/1992 | Benson et al. | 424/47 |
| 5,266,303 | 11/1993 | Myers et al. | 424/45 |

FOREIGN PATENT DOCUMENTS

| | | |
|---|---|---|
| 1081617 | 7/1980 | Canada . |
| 0331994 | 9/1989 | European Pat. Off. . |
| 0406042 | 1/1991 | European Pat. Off. . |
| 551748 | 7/1993 | European Pat. Off. . |
| 2238474 | 2/1975 | France . |

OTHER PUBLICATIONS

Martino, G.T. et al. (1992). Spray Technology & Marketing, Mar. Issue, pp. 34–39.

*Primary Examiner*—Thurman K. Page
*Assistant Examiner*—Raj Bawa
*Attorney, Agent, or Firm*—Oliff & Berridge

[57] ABSTRACT

Aqueous aerosol lacquer contains, in solution in water, a copolymer having repeating units derived from the polymerization of:

(i) least one unsaturated sulphonic acid in a proportion of 30 to 90% by weight and having the following general formula:

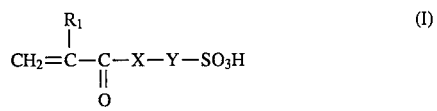

in which:

$R_1$ denotes a hydrogen atom or the $CH_3$ radical,

X denotes —O— or —NH—, and

Y denotes a linear or branched alkylene chain containing from 1 to 6 carbon atoms, and (ii) at least one N-monoalkylacrylamide or methacrylamide in a proportion of 10 to 70% by weight and having the following general formula:

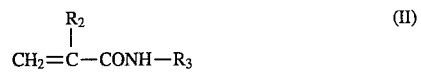

in which:

$R_2$ denotes a hydrogen atom or —$CH_3$ radical and $R_3$ denotes a linear or branched radical containing from 3 to 10 carbon atoms, the sulphonic acid functional groups of the copolymer being neutralized in a proportion of 40 to 70% with triethanolamine, and the propellent agent of the aerosol lacquer being dimethyl ether.

15 Claims, No Drawings

AQUEOUS AEROSOL LACQUER FOR SETTING HAIR

The present invention relates to a cosmetic composition in the form of an aqueous aerosol lacquer for setting hair containing, as film-forming substance, a copolymer consisting essentially of units of an unsaturated sulphonic acid and of an N-monoalkylacrylamide or methacrylamide and optionally of another monomer, the sulphonic acid functional groups of the said polymer being neutralized with the aid of triethanolamine, the propellent gas of the said lacquer being dimethyl ether.

BACKGROUND OF THE INVENTION

The present trend is to replace systematically, for ecological reasons, the halogenated propellent gases of the "Freon" type in aerosol containers for hair, but the replacement of such propellants with less harmful gases such as dimethyl ether (DME) requires a far-reaching modification of the formulations. In fact, such a replacement affects not only the ratios of the various ingredients but also the very nature of the latter, and very particularly that of the film-forming substances.

It is well known, in fact, that an aerosol lacquer for setting hair must satisfy a certain number of criteria and, among these, a good ability to lacquer the hair even in an atmosphere with a high moisture content without an effect of stickiness of the hair being observed.

It is moreover appropriate that the hair should have a natural appearance, the hair being shiny and soft and that it can be combed without producing a powdery effect.

Furthermore, the viscosity of the compositions to be sprayed must be such that it can allow a good distribution by means of the valve device.

The use, in hair-care compositions and aerosol lacquers propelled by halogenated hydrocarbons, of polymers resulting from the polymerization of sulphonic acid derivatives optionally with other monomers such as alkyl acrylate derivatives or acrylamide derivatives has been described in French Patent No. 73.27329.

This French patent, the subject of which is particularly general, does not however describe or suggest aerosol lacquers in which the carrier is water and the propellant dimethyl ether.

The use of dimethyl ether as a propellent agent for water lacquers raises, in fact, many difficulties relating to the solubility and homogeneity of the compositions.

After various investigations into many copolymers containing units derived from the polymerization of unsaturated sulphonic acids it has unexpectedly and surprisingly been found that, in order to obtain aerosol lacquers which have good cosmetic properties and a good lacquering capacity at the same time, a very strict choice is necessary, not only concerning the nature of the copolymer but also that of the neutralizing agent and of the degree of neutralization of the sulphonic acid functional groups of the copolymer.

Such a choice has made it possible, in fact to reveal an excellent solubility in water of the copolymers in combination with a good compatibility with dimethyl ether.

Furthermore, it has been found that the copolymers of the aerosol lacquers according to the invention also have to meet a very precise criterion of viscosity with a view to obtaining aerosol lacquers exhibiting good distribution.

SUMMARY OF INVENTION

The subject of the present invention is therefore an aerosol lacquer for maintaining and/or setting hair which has in solution in water, as a film-forming substance, a copolymer consisting essentially of repeat units derived from the polymerization (i) of at least one unsaturated sulphonic acid in a proportion of 30 to 90% by weight and having the following general formula:

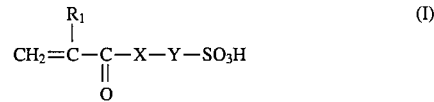

in which:

$R_1$ denotes a hydrogen atom or the —$CH_3$ radical,

X denotes —O— or —NH—, and preferably —NH—,

Y denotes a linear or branched alkylene chain containing from 1 to 6 carbon atoms, and (ii) of at least one N-monoalkylacrylamide or methacrylamide in a proportion of 10 to 70% by weight and having the following general formula:

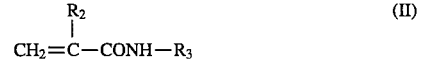

in which:

$R_2$ denotes a hydrogen atom or the —$CH_3$ radical and $R_3$ denotes a linear or branched alkyl radical containing from 3 to 10 carbon atoms, the sulphonic acid functional groups of the said polymer being neutralized in a proportion of 40 to 70% with triethanolamine, and the propellent agent of the said aerosol lacquer being dimethyl ether.

DETAILED DESCRIPTION OF PREFERRED EMBODIMENTS

Among the unsaturated sulphonic acids of general formula (I) there may be mentioned especially 2-acrylamido-2-methylpropanesulphonic acid, N-acryloyltaurine and N-methacryloyltaurine.

Among the N-monoalkylacrylamides or methacrylamides of general formula (II) there may be mentioned especially N-tert-butylacrylamide, N-tert-hexylacrylamide and N-tert-octylacrylamide.

The copolymer according to the invention preferably results from the copolymerization of an amidosulphonic acid (X=—NH—) in which the alkylene chain has from 2 to 4 carbon atoms, and in particular of 2-acrylamido-2-methylpropanesulphonic acid, in a proportion of 40 to 70% by weight and of an N-monoalkylacrylamide and, in particular, of N-tert-butylacrylamide.

Although the copolymers of the aerosol lacquers according to the invention have been defined essentially as being dipolymers, they may also be in the form of ter- or tetrapolymers.

According to this embodiment, the comonomers capable of forming the other repeat units of the copolymer may be chosen from:

1) alkyl acrylates or methacrylates in a proportion of 3 to 40% by weight and having the following general formula:

in which:

$R_4$ denotes a hydrogen atom or a —$CH_3$ radical, and $R_5$ denotes a linear or branched alkyl radical which has from 1 to 4 carbon atoms.

Among the alkyl acrylates and methacrylates of formula (III) there may be mentioned especially methyl acrylate, ethyl acrylate and butyl methacrylate.

According to a particular embodiment it is preferred to employ methyl acrylate or ethyl acrylate in a proportion of 3 to 25% by weight.

2) acrylamides and methacrylamides in a proportion of 3 to 40% by weight and having the following general formula:

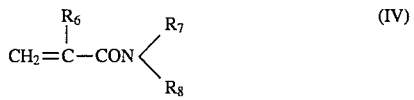

in which:

$R_6$ denotes a hydrogen atom or the —$CH_3$ radical, and
$R_7$ and $R_8$, which are identical or different, denote a hydrogen atom or an alkyl radical which has from 1 to 4 carbon atoms or $R_7$ denotes a hydrogen atom and $R_8$ denotes the radical:

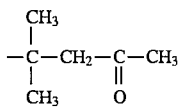

Among the acrylamides and methacrylamides of formula (IV) there may be mentioned especially dimethyl-3-oxobutylacrylamide, N,N-dimethylacrylamide and N,N-diethylacrylamide, but preferably dimethyl-3-oxobutyl acrylamide in a proportion of 3 to 25%.

Among the particularly preferred copolymers according to the invention there may be mentioned especially those containing repeat units derived from the copolymerization of:

2-acrylamido-2-methylpropanesulphonic acid (62%)/N-tert-butylacrylamide (38%), 2-acrylamido-2-methylpropanesulphonic acid (40%)/N-tert-butylacrylamide (20%)/ethyl acrylate (15%)/dimethyl-3-oxobutylacrylamide (25%), 2-acrylamido-2-methylpropanesulphonic acid (60%)/N-tert-butylacrylamide (20%)/dimethyl-3-oxobutylacrylamide (20%), 2-acrylamido-2-methylpropanesulphonic acid (60%)/N-tert-butylacrylamide (25%)/ethyl acrylate (15%), and 2-acrylamido-2-methylpropanesulphonic acid (60%)/N-tert-butylacrylamide (25%)/methyl acrylate (15%).

As indicated above, the good cosmetic properties of the aerosol lacquers according to the invention are due not only to the nature of the copolymer but also to that of the neutralizing agent employed and to the degree of neutralization of the sulphonic acid functional groups.

The investigations which have been carried out, in particular into the 2-acrylamido-2-methylpropanesulphonic acid (62%)/N-tert-butylacrylamide (38%) copolymer, have shown that when it is 50 or 100% neutralized with 2-amino-2-methylpropanol a lacquer is obtained which has a low lacquering capacity that cannot be improved by the addition of a conventional plasticizer, insofar as certain side effects are then observed, such as an effect of stickiness to the touch due to increase in the hygroscopicity.

Among the various alkanolamines, only triethanolamine has been found satisfactory as a neutralizing agent for the sulphonic acid functional groups, in a proportion of 40 to 70% of the latter.

The viscosity of the copolymers neutralized to 50% with triethanolamine, in aqueous solution containing 5% AS and measured with the Drage 2 rotor at 25° C. is preferably lower than 0.1 Pa s (100 cps).

If the viscosity of the copolymer was higher, it would then not be possible to obtain a good distribution because of the possibilities of blocking of the valve.

Since the viscosity is a direct function of the molecular weight of the copolymers, in the case of the copolymers of the lacquers according to the invention this weight is generally between 10,000 and 500,000, determined by the steric exclusion chromatography method.

In the aerosol lacquers according to the invention the copolymer as defined above is generally present in a proportion of between 2 and 25% by weight relative to the total weight of the lacquer, and preferably between 5 and 20%.

Although the neutralization of the copolymer can be carried out before its use, it is preferably performed within the actual composition when it is formed.

The carrier, namely water, is generally present in a proportion of between 63 and 88% by weight relative to the total weight of the lacquer, and preferably between 63 and 75%.

The propellent agent, namely dimethyl ether, is generally present in a proportion of between 10 and 35% by weight relative to the total weight of the lacquer, which makes it possible to produce a homogeneous solution.

The aerosol lacquers according to the invention may also contain other conventional cosmetic ingredients such as softening agents, perfumes, silicones, sun screens, dyes, stabilizers, antifoamagents, vitamins and proteins.

According to the invention it is desirable that the vapour pressure in the aerosol container should be between approximately 2.5 and 5 bars at 25° C.

The aerosol container in which the composition is packaged may be of the conventional type or may be optionally fitted with an additional gas connection with a view to obtaining a spray of finer quality.

The copolymers of the aerosol composition according to the invention are, for the most part, known and can be obtained by conventional polymerization methods, especially in solution in a solvent.

Among the polymerization initiators which can be employed in the polymerization process there may be mentioned in particular: benzoyl peroxide, azobisisobutyronitrile, tert-butyl 2-ethylperhexanoate, tert-butyl perpivalate and di(4-tert-butylcyclohexyl) peroxydicarbonate, these initiators being employed either by themselves or mixed.

The quantity of initiator is generally between 0.1 and 6% by weight relative to the total weight of the monomers to be polymerized. The polymerization reaction is preferably performed at a temperature of between 45° and 100° C. and more particularly at the reflux temperature of the reaction mixture.

The reaction time is preferably between 6 and 24 hours.

A number of examples of preparation of the copolymers and examples of aerosol lacquers will now be given by way of illustration.

EXAMPLES OF PREPARATION OF THE COPOLYMERS

EXAMPLE 1

Copolymer of 62% by weight 2-acrylamido-2-methylpropanesulphonic acid (AMPS) and 38% b weight N-tert-butylacrylamide (NTBA)

38 g of N-tert-butylacrylamide (NTBA), 0.5 g of azobisisobutyronitrile (AIBN) and 227.5 g of ethanol are introduced in succession into a 2-liter reactor and are stirred until dissolved. At the same time, 62 g of AMPS are separately dissolved in 122.5 g of demineralized water. The aqueous solution of AMPS is poured into the reactor while stirring is maintained with nitrogen bubbling. After mixing, the mixture is heated with stirring and nitrogen bubbling at 70° C. and these conditions are maintained for 5 hours.

At the end of this time and return to ambient temperature, the solution is concentrated in a rotary evaporator. It is purified by dialysis by employing membranes which remove the copolymers of MW<6000.

Yield obtained: 85%

Acid value on the freeze-dried product: 160 mg KOH/g of product)

EXAMPLES 2 TO 5

The copolymers of Table I were prepared by operating essentially as in Example 1.

First of all, AMPS is dissolved in water and the aqueous solution obtained is then poured into the reactor containing the remaining monomers, the ethanol and the initiator (AIBN).

After polymerization at 70° C. for 18 hours the polymerization solution is concentrated in the rotary evaporator to remove the ethanol. After three days' dialysis on membranes which remove the copolymers of MW of approximately 6000, freeze drying is performed.

| Copolymer of Example 2 | | 5.6 g |
|---|---|---|
| Triethanolamine | q.s. for 50% neutralization | |
| Perfume | q.s. | |
| Stabilizer | q.s. | |
| Dimethyl ether | | 30 g |
| Water | q.s. | 100 g |

EXAMPLE C

An aerosol lacquer for hair which has the following composition was prepared using the same operating method as described in Example 1:

| Copolymer of Example 3 | | 6.3 g |
|---|---|---|
| Triethanolamine | q.s. for 50% neutralization | |
| Perfume | q.s. | |
| Stabilizer | q.s. | |
| Dimethyl ether | | 30 g |
| Water | q.s. | 100 g |

EXAMPLE D

An aerosol lacquer for hair which has the following composition was prepared using the same operating method as described in Example 1:

TABLE I

| | | Quantities of monomers normalized to 100 g | | | | Quantity of solvents per 100 g monomers | | | | |
|---|---|---|---|---|---|---|---|---|---|---|
| Examples | AMPS | N-tert-butylacryl-amide | Methyl acrylate | Ethyl acrylate | Dimethyl-3-oxo-butylacryl-amide | Ethanol | Water | AIBN (*) | Yield | Acid value |
| 2 | 40 g | 20 g | — | 15 g | 25 g | 150 g | 150 g | 0.5 g | 88% | 130 |
| 3 | 60 g | 20 g | — | — | 20 g | 150 g | 150 g | 0.5 g | 86.50% | 156.5 |
| 4 | 60 g | 25 g | — | 15 g | — | 150 g | 150 g | 0.5 g | 93% | 190 |
| 5 | 60 9 | 25 g | 15 g | — | — | 60 g | 60 g | 0.5 g | 65% | 155 |

(*) quantity per 100 g of monomers

EXAMPLES OF AEROSOL LACQUERS

EXAMPLE A

An aerosol lacquer for hair is prepared by packaging, in a suitable aerosol container, 8.4 g of the copolymer of Example 1, which is 60% neutralized (according to the acid value) by adding triethanolamine, a perfume, a stabilizer in sufficient quantity, and a sufficient quantity of water to make up to 70 g.

30 g of dimethyl ether are then introduced by conventional methods and the valve is fitted and the container closed hermetically (4.6 bars pressure).

The valve may be of the type with an additional gas connection with a view to obtaining a spray of finer quality.

When the lacquer is applied to natural hair or to sensitized hair it is found to have an excellent lacquering capacity and not not to produce any effect of stickiness when applied and after drying.

EXAMPLE B

An aerosol lacquer for hair which has the following composition was prepared using the same operating method as described in Example 1:

| Copolymer of Example 4 | | 2.8 g |
|---|---|---|
| Triethanolamine | q.s. for 70% neutralization | |
| Perfume | q.s. | |
| Stabilizer | q.s. | |
| Dimethyl ether | | 30 g |
| Water | q.s. | 100 g |

EXAMPLE E

An aerosol lacquer for hair which has the following composition was prepared using the same operating method as described in Example 1:

| Copolymer of Example 5 | | 1.8 g |
|---|---|---|
| Triethanolamine | q.s. for 60% neutralization | |
| Perfume | q.s. | |
| Stabilizer | q.s. | |
| Dimethyl ether | | 30 g |
| Water | q.s. | 100 g |

We claim:
1. A water based aerosol hair lacquer containing in an aerosol container a homogeneous solution consisting essentially of:

(a) 63 to 88% by weight of a carrier consisting of water,
(b) 10 to 35% by weight of a propellent consisting of dimethyl ether, and
(c) 2 to 25% by weight relative to the total weight of the lacquer of a water-soluble film-forming copolymer, said copolymer comprising repeating units resulting from the polymerization of:
 (i) 30 to 90% by weight of an unsaturated sulphonic acid having the formula:

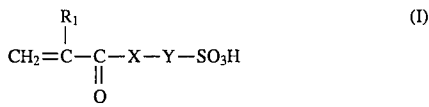
(I)

in which:
 $R_1$ represents a hydrogen atom or —$CH_3$,
 X represents —O— or —NH—, and
 Y represents a linear or branched alkylene chain having from 1 to 6 carbon atoms, and
 (ii) 10 to 70% by weight of N-monoalkylacrylamide or methacrylamide having the formula:

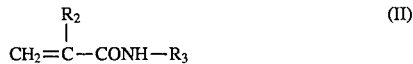
(II)

in which:
 $R_2$ represents a hydrogen atom or —$CH_3$ and
 $R_3$ represents a linear or branched radical having from 3 to 10 carbon atoms, the sulphonic acid functions of said copolymer being neutralized in a proportion from 40 to 70% with triethanolamine.

2. Aerosol lacquer according to claim 1, wherein the unsaturated sulphonic acid of formula (I) is selected from the group consisting of 2-acrylamido-2-methylpropanesulphonic acid, N-acryloyltaurine and N-methacryloyltaurine.

3. Aerosol lacquer according to claim 1, wherein the N-monoalkylacrylamide or methacrylamide of formula (II) is selected from the group consisting of N-tert-butylacrylamide, N-tert-hexylacrylamide and N-tert-octylacrylamide.

4. Aerosol lacquer according to claim 1, wherein the copolymer results from the copolymerization of an amidosulphonic acid in which the alkylene chain has from 2 to 4 carbon atoms, in a proportion of 40 to 70% by weight, and of an N-monoalkylacrylamide.

5. Aerosol lacquer according to claim 1, wherein the copolymer further contains repeating units derived from the copolymerization of an alkyl acrylate or methacrylate in a proportion of 3 to 40% by weight and having the following general formula:

(III)

in which:
$R_4$ denotes a hydrogen atom or a —$CH_3$ radical, and
$R_5$ denotes a linear or branched alkyl radical which has from 1 to 4 carbon atoms.

6. Aerosol lacquer according to claim 5, wherein the alkyl acrylate or methacrylate of formula (III) is selected from the group consisting of methyl acrylate, ethyl acrylate and butyl methacrylate.

7. Aerosol lacquer according to claim 5, wherein the alkyl acrylate or methacrylate units are present in a proportion of 3 to 25% by weight of the polymer.

8. Aerosol lacquer according to claim 1, wherein the polymer further contains repeating units derived from the polymerization of an acrylamide or methacrylamide in a proportion of 3 to 40% by weight and having the following general formula:

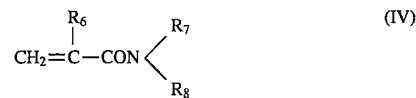
(IV)

in which:
$R_6$ denotes a hydrogen atom or the —$CH_3$ radical, and
$R_7$ and $R_8$, which are identical or different, denote a hydrogen atom or an alkyl radical which has from 1 to 4 carbon atoms or $R_7$ denotes a hydrogen atom and $R_8$ denotes the radical:

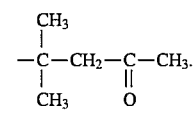

9. Aerosol lacquer according to claim 8, wherein the acrylamide or methacrylamide of formula (IV) is selected from the group consisting of dimethyl-3-oxobutylacrylamide, N,N-dimethylacrylamide and N,N-diethylacrylamide.

10. Aerosol lacquer according to claim 8, wherein the acrylamide or methacrylamide units are present in a proportion of 3 to 25% by weight of the copolymer.

11. An aerosol lacquer according to claim 1, wherein the copolymer is selected from the group consisting of:
 62% 2-acrylamido-2-methylpropanesulphonic acid/38% N-tert-butylacrylamide,
 40% 2-acrylamido-2-methylpropanesulphonic acid/20% N-tert-butylacrylamide/15% ethyl acrylate/25% dimethyl-3-oxobutylacrylamide,
 60% 2-acrylamido-2-methylpropanesulphonic acid/20% N-tert-butylacrylamide, 20% dimethyl-3-oxobutylacrylamide,
 60% 2-acrylamido-2-methylpropanesulphonic acid/25% N-tert-butylacrylamide/15% ethyl acrylate, and
 60% 2-acrylamido-2-methylpropanesulphonic acid/25% N-tert-butylacrylamide, 15% methyl acrylate.

12. Aerosol lacquer according to claim 1, wherein the copolymer is present in a proportion of between 5 and 20% by weight relative to the total weight of the lacquer.

13. Aerosol lacquer according to claim 1, wherein the water is present in a proportion of between 63 and 88% by weight relative to the total weight of the lacquer.

14. Aerosol lacquer according to claim 1, which further contains at least one conventional cosmetic ingredient selected from the group consisting of softening agents, perfumes, silicones, sun screens, dyes, stabilizers, anti-foam agents, vitamins and proteins.

15. Aerosol lacquer according to claim 1, wherein said lacquer is contained in an aerosol container.

* * * * *